(12) United States Patent
Casey et al.

(10) Patent No.: US 12,011,911 B2
(45) Date of Patent: Jun. 18, 2024

(54) ISOTROPIC NON-AQUEOUS ELECTRODE SENSING MATERIAL

(71) Applicant: FLEXcon Company, Inc., Spencer, MA (US)

(72) Inventors: James Casey, East Brookfield, MA (US); Richard Skov, Spencer, MA (US); Kenneth Burnham, Warren, MA (US); Patrice Mariucci, Monson, MA (US); Pamela Fitzgerald, Brookfield, MA (US); John Pennace, Spencer, MA (US)

(73) Assignee: FLEXCON COMPANY, INC., Spencer, MA (US)

( * ) Notice: Subject to any disclaimer, the term of this patent is extended or adjusted under 35 U.S.C. 154(b) by 249 days.

(21) Appl. No.: 17/212,350

(22) Filed: Mar. 25, 2021

(65) Prior Publication Data
US 2022/0274372 A1 Sep. 1, 2022

Related U.S. Application Data

(60) Provisional application No. 62/994,558, filed on Mar. 25, 2020.

(51) Int. Cl.
*B32B 5/22* (2006.01)
*B32B 5/02* (2006.01)
(Continued)

(52) U.S. Cl.
CPC .............. *B32B 5/022* (2013.01); *B32B 27/12* (2013.01); *C08K 3/04* (2013.01); *D06N 3/0011* (2013.01);
(Continued)

(58) Field of Classification Search
CPC ... B32B 5/022; B32B 27/12; B32B 2260/021; B32B 2260/046; B32B 2262/106;
(Continued)

(56) References Cited

U.S. PATENT DOCUMENTS 3,911,906 A   10/1975   Reinhold, Jr.
4,008,721 A   2/1977    Burton
(Continued)

FOREIGN PATENT DOCUMENTS

CA   2477615 A1   1/2006
CN   85105901 A   1/1987
(Continued)

OTHER PUBLICATIONS

Communication pursuant to Rules 161(1) and 162 EPC issued by the European Patent Office in related European Patent Application No. 21719428.1 dated Jan. 2, 2022, 3 pages.
(Continued)

*Primary Examiner* — Matthew D Matzek
(74) *Attorney, Agent, or Firm* — NORTON ROSE FULBRIGHT US LLP

(57) ABSTRACT

A non-aqueous isotropic electrically conductive signal receptive composite is disclosed comprising a continuous conductive material, with a top surface and a bottom surface with both surfaces substantially covered by a dielectric polymer material with a polar material within the dielectric polymer.

21 Claims, 17 Drawing Sheets

(51) Int. Cl.
   *B32B 27/12* (2006.01)
   *C08K 3/04* (2006.01)
   *D06N 3/00* (2006.01)

(52) U.S. Cl.
   CPC ...... *D06N 3/0059* (2013.01); *B32B 2260/021* (2013.01); *B32B 2260/046* (2013.01); *B32B 2262/106* (2013.01); *B32B 2307/202* (2013.01); *C08K 2201/001* (2013.01); *D06N 2201/087* (2013.01); *D06N 2207/123* (2013.01); *D06N 2209/041* (2013.01)

(58) Field of Classification Search
   CPC ........ B32B 2307/202; C08K 2201/001; C08K 3/04; D06N 2201/087; D06N 2207/123; D06N 2209/041; D06N 3/0011; D06N 3/0059; A61B 2562/125; A61B 5/257; A61B 5/263; C09J 2301/124; C09J 2301/302; C09J 2301/314; C09J 2433/00; C09J 7/28
   USPC ............................................. 442/1; 428/343
   See application file for complete search history.

(56) References Cited

U.S. PATENT DOCUMENTS

| | | | |
|---|---|---|---|
| 4,063,352 A | 12/1977 | Bevilacqua | |
| 4,074,000 A | 2/1978 | Hankee et al. | |
| 4,170,677 A | 10/1979 | Hutcheson | |
| 4,188,449 A | 2/1980 | Lu et al. | |
| 4,293,665 A | 10/1981 | Zalucha et al. | |
| 4,352,359 A | 10/1982 | Larimore et al. | |
| 4,353,372 A | 10/1982 | Ayer | |
| 4,417,174 A | 11/1983 | Kamijo et al. | |
| 4,422,461 A | 12/1983 | Glumac | |
| 4,460,369 A | 7/1984 | Seymour | |
| 4,548,862 A | 10/1985 | Hartman | |
| 4,581,821 A | 4/1986 | Cahalan et al. | |
| 4,687,968 A | 8/1987 | Frayer | |
| 4,731,282 A | 3/1988 | Tsukagoshi et al. | |
| 4,750,482 A * | 6/1988 | Sieverding | C09J 7/10 602/56 |
| 4,798,773 A | 1/1989 | Yasukawa et al. | |
| 4,816,717 A | 3/1989 | Harper et al. | |
| 4,848,353 A | 7/1989 | Engel | |
| 4,852,571 A | 8/1989 | Gadsby et al. | |
| 5,082,595 A | 1/1992 | Glackin | |
| 5,120,325 A | 6/1992 | Dow, Jr. | |
| 5,120,422 A | 6/1992 | Liu et al. | |
| 5,143,071 A | 9/1992 | Keusch et al. | |
| 5,311,658 A | 5/1994 | Schimizu | |
| 5,321,069 A | 6/1994 | Owens | |
| 5,338,490 A | 8/1994 | Dietz et al. | |
| 5,362,420 A | 11/1994 | Itoh et al. | |
| 5,388,026 A | 2/1995 | Kanbara et al. | |
| 5,409,777 A | 4/1995 | Kennedy et al. | |
| 5,421,982 A | 6/1995 | Ikeda et al. | |
| 5,450,845 A | 9/1995 | Axelgaard | |
| 5,479,070 A | 12/1995 | Murakami | |
| 5,552,679 A | 9/1996 | Murasko | |
| 5,645,062 A | 7/1997 | Anderson et al. | |
| 5,800,685 A | 9/1998 | Perrault | |
| 5,821,691 A | 10/1998 | Richie et al. | |
| 5,906,720 A | 5/1999 | Ferguson et al. | |
| 5,932,339 A | 8/1999 | Sakurai et al. | |
| 6,121,508 A | 9/2000 | Bischof et al. | |
| 6,134,480 A | 10/2000 | Minogue | |
| 6,198,216 B1 | 3/2001 | Kosa et al. | |
| 6,207,077 B1 | 3/2001 | Burnell-Jones | |
| 6,214,251 B1 | 4/2001 | Wu et al. | |
| 6,232,366 B1 | 5/2001 | Wang et al. | |
| 6,327,487 B1 | 12/2001 | Stratbucker | |
| 6,342,561 B1 | 1/2002 | Engel et al. | |
| 6,432,516 B1 | 8/2002 | Teraski et al. | |
| 6,576,712 B2 | 6/2003 | Feldstein et al. | |
| 6,687,524 B1 | 2/2004 | Svejk | |
| 7,076,282 B2 | 7/2006 | Munro et al. | |
| 7,169,250 B2 | 1/2007 | Kim et al. | |
| 7,651,638 B2 | 1/2010 | Segall et al. | |
| 7,981,495 B2 | 7/2011 | Kim et al. | |
| 8,673,184 B2 | 3/2014 | Burnham et al. | |
| 8,788,009 B2 | 7/2014 | Greene et al. | |
| 8,792,957 B2 | 7/2014 | Greene et al. | |
| 9,775,235 B2 | 9/2017 | Burnham et al. | |
| 9,818,499 B2 | 11/2017 | Burnham et al. | |
| 9,947,432 B2 | 4/2018 | Burnham et al. | |
| 2001/0038925 A1 | 11/2001 | Barton et al. | |
| 2002/0037977 A1 | 3/2002 | Feldstein et al. | |
| 2003/0102154 A1 | 6/2003 | Haba | |
| 2004/0000663 A1 | 1/2004 | Segall et al. | |
| 2004/0073104 A1 | 4/2004 | Brun del Re et al. | |
| 2004/0210122 A1 | 10/2004 | Sieburg | |
| 2004/0212386 A1 | 10/2004 | Lin | |
| 2005/0096574 A1 | 5/2005 | Wibaux | |
| 2005/0107714 A1 | 5/2005 | Matsumura et al. | |
| 2006/0069320 A1 | 3/2006 | Wolff et al. | |
| 2006/0074284 A1 | 4/2006 | Juola et al. | |
| 2007/0010750 A1 | 1/2007 | Ueno et al. | |
| 2007/0032719 A1 | 2/2007 | Menon et al. | |
| 2007/0035808 A1 | 2/2007 | Amundson et al. | |
| 2008/0197853 A1 | 8/2008 | Swift et al. | |
| 2008/0208063 A1 | 8/2008 | Brauers et al. | |
| 2008/0221424 A1 | 9/2008 | Segall et al. | |
| 2008/0311378 A1 | 12/2008 | Simpson | |
| 2009/0005667 A1 | 1/2009 | Cui et al. | |
| 2009/0038832 A1 | 2/2009 | Chaffins et al. | |
| 2009/0078747 A1 | 3/2009 | Park et al. | |
| 2009/0224422 A1 | 9/2009 | Dubin | |
| 2010/0016702 A1 | 1/2010 | Greene et al. | |
| 2010/0036230 A1 | 2/2010 | Greene et al. | |
| 2010/0189952 A1 | 7/2010 | Segall et al. | |
| 2010/0310866 A1 * | 12/2010 | Yamamoto | C09J 7/385 524/556 |
| 2010/0327232 A1 | 12/2010 | Yamamoto et al. | |
| 2011/0105875 A1 | 5/2011 | Segall et al. | |
| 2011/0132537 A1 * | 6/2011 | Choi | C09J 7/00 156/60 |
| 2012/0064325 A1 * | 3/2012 | Fumoto | C09J 7/29 428/354 |
| 2012/0085580 A1 | 4/2012 | Yamamoto et al. | |
| 2012/0145315 A1 | 6/2012 | Knaapila et al. | |
| 2012/0224285 A1 | 9/2012 | Svasand et al. | |
| 2013/0092881 A1 | 4/2013 | Burnham et al. | |
| 2013/0092882 A1 | 4/2013 | Burnham et al. | |
| 2013/0118773 A1 * | 5/2013 | Liu | C09J 9/02 174/117 F |
| 2014/0049684 A1 | 4/2014 | Cheng et al. | |
| 2014/0124711 A1 | 5/2014 | Burnham et al. | |
| 2014/0221807 A1 | 8/2014 | Park et al. | |
| 2014/0246628 A1 | 9/2014 | Anhalt et al. | |
| 2014/0262446 A1 | 9/2014 | Burnham et al. | |
| 2014/0296684 A1 | 10/2014 | Burnham et al. | |
| 2014/0296685 A1 | 10/2014 | Burnham et al. | |
| 2015/0282312 A1 | 10/2015 | Burnham et al. | |
| 2016/0027548 A1 | 1/2016 | Burnham et al. | |
| 2018/0042108 A1 | 2/2018 | Burnham et al. | |

FOREIGN PATENT DOCUMENTS

| | | |
|---|---|---|
| CN | 1402768 A | 3/2003 |
| CN | 1871537 A | 11/2006 |
| CN | 101188969 A | 5/2008 |
| CN | 101953026 A | 1/2011 |
| CN | 102098959 A | 6/2011 |
| CN | 101238189 B | 12/2012 |
| DE | 2935238 A1 | 3/1981 |
| DE | 19922999 A1 | 11/2000 |
| EP | 1674036 A1 | 6/2006 |
| EP | 2799007 A1 | 11/2014 |
| GB | 2115431 A | 9/1983 |
| JP | S5719904 A | 2/1982 |
| JP | S6222383 A | 1/1987 |

(56) References Cited

FOREIGN PATENT DOCUMENTS

| | | |
|---|---|---|
| JP | H02257590 A | 10/1990 |
| JP | H04503831 A | 7/1992 |
| JP | 7011247 B2 | 1/1995 |
| JP | H0788971 A | 4/1995 |
| JP | H08315883 A | 11/1996 |
| JP | H08315946 A | 11/1996 |
| JP | H09508290 A | 8/1997 |
| JP | H10247536 A | 9/1998 |
| JP | 2000508825 A | 7/2000 |
| JP | 2000235877 A | 8/2000 |
| JP | 2000260561 A | 9/2000 |
| JP | 2001078974 A | 3/2001 |
| JP | 2005110801 A | 4/2005 |
| JP | 2008203256 A | 9/2008 |
| JP | 2009503235 A | 1/2009 |
| JP | 2010053250 A | 3/2010 |
| JP | 2010102859 A | 5/2010 |
| JP | 2011528578 A | 11/2011 |
| JP | 2012062342 A | 3/2012 |
| JP | 2012531026 A | 12/2012 |
| JP | 2015503178 A | 1/2015 |
| JP | 2016519390 A | 6/2016 |
| JP | 2020000853 A | 1/2020 |
| NO | 20092381 L | 12/2010 |
| WO | 9111493 A2 | 8/1991 |
| WO | 9531491 A1 | 11/1995 |
| WO | 9724149 A1 | 7/1997 |
| WO | 0029493 A1 | 5/2000 |
| WO | 0174119 A1 | 10/2001 |
| WO | 0219020 A1 | 3/2002 |
| WO | 03087250 A1 | 10/2003 |
| WO | 2005032268 A2 | 4/2005 |
| WO | 2006131855 A2 | 12/2006 |
| WO | 2010009385 A1 | 1/2010 |
| WO | 2010151141 A1 | 12/2010 |
| WO | 2010151142 A1 | 12/2010 |
| WO | 2010151148 A1 | 12/2010 |
| WO | 2012076612 A1 | 6/2012 |
| WO | 2012081991 A1 | 6/2012 |
| WO | 2012081992 A2 | 6/2012 |
| WO | 2012085084 A3 | 6/2012 |
| WO | 2012085105 A1 | 6/2012 |

OTHER PUBLICATIONS

Notification Concerning Transmittal of International Preliminary Report on Patentability and International Preliminary Report on Patentbility issued in related international application No. PCT/US2021/024083 by the International Bureau of WIPO dated Sep. 22, 2022, 12 pages.

International Search Report and Written Opinion of the International Searching Authority (the European Patent Office) issued in related International Application No. PCT/US2021/024083 dated Aug. 30, 2021, 17 pages.

Annex to Form PCT/ISA/206, Communication Relating to the Results of the Partial International Search, issued by the International Searching Authority (the European Patent Office) in related International Application No. PCT/US2021/024083 dated Jul. 8, 2021, 9 pages.

Notice on Reasons for Refusal issued by the Japanese Patent Office in related Japanese Patent Application No. 2022-558039 dated Nov. 17, 2023, 6 pages.

Examination report No. 1 issued by the Australian Patent Office in related Australian Patent Application No. 2021241676 dated Nov. 14, 2023, 5 pages.

Allred et al., Surface Modification of Exfoliated Graphite Nano-Reinforcements, Ref: Proc. 38th SAMPE Tech. Conf., Dallas, TX, Nov. 7-9, 2006, 14 pages.

Kim et al., Anisotropic conductivity of magnetic carbon nanotubes embedded in epoxy matrices, Carbon 49, 2011, pp. 54-61, ScienceDirect.

Kim, Thermo-physical responses of polymeric composites tailored by electric field, Composites Science and Technology 65, 2005, pp. 1728-1735.

Prasse et al., Electric anisotropy of carbon nanofibre/epoxy resin composites due to electric field induced alignment, Composites Science and Technology 63, 2003, pp. 1835-1841.

Ramkumar et al., A Novel Anisotropic Conductive Adhesive for Lead-Free Surface mount Electronics Packaging, Journal of Electronic Packaging, Jun. 2007, vol. 129, pp. 149-156.

Ramkumar et al., Influence of Process Parameters on Component Assembly and Drop Test Performance using a Novel Anisotropic Conductive Adhesive for Lead-free Surface mount Assembly, Center for Electronics Manufacturing and Assembly, Rochester Institute of Technology, Rochester, NY, 2008 Electronic Components and Technology Conference, pp. 225-233.

Searle et al., A direct comparison of wet, dry and insulating bioelectric recording electrodes, Physiol. Meas. 21, 2000, pp. 271-283.

Solid surface energy data (SFE) for common polymers, retrieved from http://www.surface-tension.de/solid-surface-energy.htm on Sep. 1, 2010, 2 pages.

* cited by examiner

| Test | AC Impedance | | Defibrillation Overload Recovery | | DC Offset Voltage | Combined Offset Instability and Internal Noise* | Bias Current Tolerance |
|---|---|---|---|---|---|---|---|
| Units | Kilo Ohms | Kilo Ohms | milli Volts | milli Volts per second | milli Volts | micro Volts | milli Volts |
| LIMIT | 2 (Ave 12) | 3 (Max Single) | 100 | 1 | 100 | 150 | 100 |
| READING (n=3) | 0.754 | 0.811 | 17 | 0.9 | 0 | 17 | 12 |
| PASS/FAIL | PASS | PASS | PASS | PASS | PASS | PASS | PASS |
| Description | Average value of 10 Hz impedance for 12 electrode pairs | Individual pair 10 Hz Impedance | Defibrillation overload recovery (polarization potential) | Rate of change of polarization potential | Offset Voltage | Combined offset instability and internal noise | DC Voltage offset |

Adhesive: Silver Mactrode +
Configurations single - pair / tab - snap
PSA Dims: 7/8" x 7/8"

| Test | AC Impedance | | Defibrillation Overload Recovery | | DC Offset Voltage | Combined Offset Instability and Internal Noise* | Bias Current Tolerance |
|---|---|---|---|---|---|---|---|
| | | | | | Adhesive: G4, Carbon Veil 20352A 4gsm; 0% Arquad; | Film/Ctg: PM100C EXV-468BK 125 Ohms per square ctg. Activation Settings: None | Bridge: Yes / No (3/8" dia carbon acrylic) Gen: 1 2 3 4 ACTAL | PSA Dims: 1" x 1" x 2 mils Configurations single - pair / tab - snap |
| Units | Kilo Ohms | Kilo Ohms | milli Volts | milli Volts per second | Kilo Ohms | milli Volts | micro Volts | milli Volts |
| LIMIT | 2 (Ave 12) | 3 (Max Single) | 100 | 1 | 3 | 100 | 150 | 100 |
| READING (n=3) | 0.159 | 0.168 | 0 | 0.1 | 0.168 | 0 | 10 | 0 |
| PASS/FAIL | PASS | PASS | PASS | PASS | PASS | PASS | PASS | PASS |
| Description | Average value of 10 Hz impedance for 12 electrode pairs | Individual pair 10 Hz impedance | Defibrillation overload recovery (polarization potential) | Rate of change of polarization potential | After test, 10Hz electrode impedance | Offset Voltage | Combined offset instability and internal noise *3~100 Hz | DC Voltage offset |

FIG. 13

| Test | AC Impedance | | Defibrillation Overload Recovery | | DC Offset Voltage | Combined Offset Instability and Internal Noise* | Bias Current Tolerance |
|---|---|---|---|---|---|---|---|
| Units | Kilo Ohms | Kilo Ohms | milli Volts | milli Volts per second | milli Volts | micro Volts | milli Volts |
| LIMIT | 2 (Ave 12) | 3 (Max Single) | 100 | 1 | 100 | 150 | 100 |
| READING (n=3) | 0.141 | 0.152 | 0 | 0.1 | 0 | 11 | 0 |
| PASS/FAIL | PASS | PASS | PASS | PASS | PASS | PASS | PASS |
| Description | Average value of 10 Hz impedance for 12 electrode pairs | Individual pair 10 Hz impedance | Defibrillation overload recovery (polarization potential) | Rate of change of polarization potential | After test, 10Hz electrode impedance | Combined offset instability and internal noise | DC Voltage offset |

Adhesive: G4; 15% Arquad;
Carbon Veil 20352A 4gsm;
Film/Ctg: PM100C EXV-468BK
125 Ohms per square ctg.
Activation Settings: None
Bridge: Yes / No
(3/8" dia carbon acrylic)
Gen: 1 2 3 4
ACTAL
Configurations
single - pair / tab - snap
PSA Dims: 1" x 1" x 2 mils Offset Voltage

| Electrode to Skin Impedance Testing - QuadTech 7600 Plus LCR 2kHz .1v | | | | | | | | | |
|---|---|---|---|---|---|---|---|---|---|
| Test Subject = Ken B. | | | | | | | | | |
| (kb) 1" Tab Electrodes; Film = PM100C EXV-468BK125 Ohms/square; PSA = Gen 4 | DATE | RH & TEMP (% & °F) | Electrode Location (LA,RA,LL,RL) | Skin Prep (y/n) | Immediate | 1 min | 2 min (kΩ) | 3 min | 4 min | 5 min |
| Carbon Veil = Technical Fibre Products # 20352A 4gsm | | | | | | | | | | |
| Carbon Veil; Arquad HTL8-MS 15% | 10/1/2019 | 50%RH & 74F | RA | no | 27 | 24 | 23 | 18 | 17 | 16 |

FIG. 16

GEN 4 WITHOUT ARQUARD (1b & 1f)

GEMS IT HAC1200   FLEXCON

Lead failure RA.

I

II

III

AUR

AUL

AUF

Oct. 01.2019   01:24:45 PM   25nm/s   10nm/mU   60Hz   0.04 - 150Hz   6 Lead   US.21 M121 (2)

FIG. 19

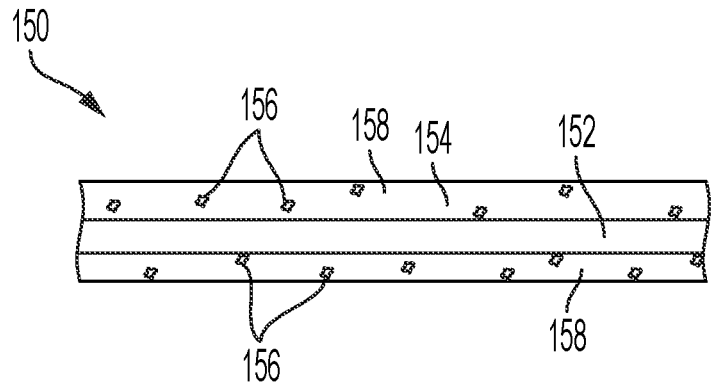
FIG. 22
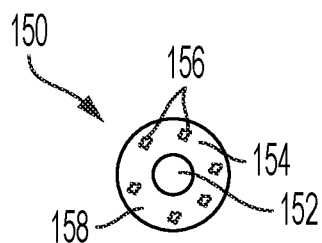
FIG. 23
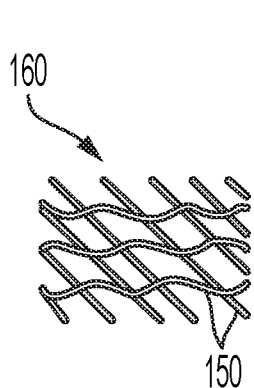    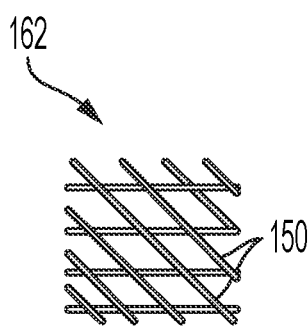    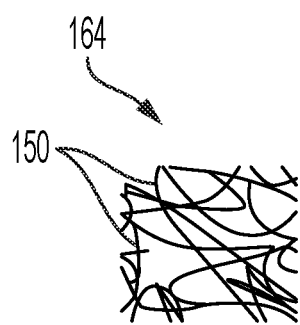
FIG. 24A           FIG. 24B           FIG. 24C

ISOTROPIC NON-AQUEOUS ELECTRODE SENSING MATERIAL

PRIORITY

The present application claims priority to U.S. Provisional Patent Application No. 62/994,558 filed Mar. 25, 2020, the disclosure of which is hereby incorporated by reference in its entirety.

BACKGROUND

The invention generally relates to sensor systems, and relates in particular to sensor systems for detecting and transferring electrical signals.

Traditionally, to pick up biomedical signals such as electrocardiogram (ECG or EKG) signals, surface electromyography (sEMG) signals and electrodermal activity (EDA) signals, various forms of ionically conductive mediums (e.g., such as hydrogels) have been used. These aqueous based signal capturing composites generally operate by relying on dissolved elements (such as salts) in the aqueous based material to ionically conduct electricity. Salts, such as sodium or potassium chloride, readily dissolve when in an aqueous medium, and their ions dissociate (separate into positive and negative ions). The dissociated ions may then convey an electrical current or signal. For this reason, salts have long been added to water, which then may be added to polymeric and elastomeric materials, to provide good electrical conductivity.

For example, U.S. Pat. No. 6,121,508 discloses a pressure sensitive adhesive hydrogel for use in a biomedical electrode. The hydrogel material is disclosed to include at least water, potassium chloride and polyethylene glycol, and is disclosed to be electrically conductive. U.S. Pat. No. 5,800,685 also discloses an electrically conductive adhesive hydrogel that includes water, salt, an initiator or catalyst and a cross linking agent. The use of such hydrogels however, also generally requires the use of a conductive, low resistance, surface at one side of the hydrogel (away from the patient) that is capable of receiving the ionically conductive charge, such as silver / silver chloride, which is relatively expensive.

While these hydrogel/adhesives can have good electrically conductive properties, they often have only fair adhesion properties. Another downside is that the electrical conductivity changes with changes in water content, such as changes caused by evaporation, requiring that the hydrogels be maintained in a sealed environment prior to use, and then used for a limited period of time only due to evaporation. The amount of water in such composites therefore, significantly impacts the electrical properties. This presents challenges with respect to shelf life and storage environments with the aqueous based electrodes because even sealed packaging may permit some amount of evaporation over time.

Alternate technologies have been developed as taught in U.S. Pat. Nos. 7,651,638, 8,788,009, 8,792,957, 8,673,184, 9,818,499, and 9775,235. Certain of the alternative technologies are based, in part, on non-aqueous based systems utilizing an organic polar compound that is substantially dispersed in a dielectric organic polymer. Depending upon the dielectric polymer chosen, such composites can also function as pressure sensitive adhesives (PSAs) to facilitate placement on a patient. Further, by careful selection of the PSA, adhesion levels can be adjusted applications from long term bonding to the skin, to less aggressive adhesion for neonatal or geriatric patients. The combination of the polar material with the polymeric dielectric material needs to avoid phase separation over time and temperature as well as when subjected to particularly high humidity conditions.

The design of an electrically conductive PSA has long presented challenges at least because adhesive strength and flexibility generally decrease with an increased presence of electrically conductive material. The materials that are typically used (added) to provide good electrical conductivity are generally less flexible and inhibit adhesion. A conventional way to prepare a conductive coating is to fill a polymeric material with conductive particles, e.g., graphite, silver, copper, etc., then coat, dry and cure the polymeric binder. In these cases the conductive particles are in such a concentration that there is a conductive network formed when the particles are each in physical contact with at least one other neighboring particle. In this way, a conductive path is provided through the composite.

For pressure sensitive adhesives, however, if the particle concentration is high enough to form a network in which particle-to-particle contact is maintained then there is little chance that the polymer (e.g., elastomer) system of the PSA component is present in high enough concentrations to flow out to make sufficient surface-to-surface contact between the substrates and an electrode, i.e., act as an adhesive. Conversely, if the PSA component is in sufficient concentration to make sufficient surface contact to the substrate, the PSA would have to interrupt adjacent conductive particles such that particle-to-particle contact is disrupted, adversely affecting electrical conductivity.

Another type of electrically conductive PSA includes conductive spherical particles with diameters equal to or greater than the thickness of the PSA. In this fashion the signal or current may be carried along the surface of the particles, thus providing current flow anisotropically in the thickness dimension of the adhesive. The continuity of the adhesive however, may be compromised due to the volume of the large spherical particles.

U.S. Pat. No. 5,082,595 discloses an electrically conductive pressure sensitive adhesive that includes carbon particles, and the conductive adhesive is disclosed to be prepared by incorporating black filler (carbon) into the pressure sensitive adhesive in such a manner as to impart electrical conductivity, yet have a concentration low enough to avoid adversely affecting the physical properties (such as tack) of the adhesive. In particular, this patent states that a slurry of the carbon black in an organic solvent is formed under mild agitation or stirring in the absence of high shear, so that carbon structures are thereby formed. The mixture may then be introduced into an adhesive. Such a composite, however, may not provide sufficient adhesiveness and conductivity in certain applications. Such composites may also include areas with relatively greater or lesser concentrations of conductive material. Certain conductive polymeric and elastomeric materials that include conductive particles in concentration within the polymeric or elastomeric material, may therefore exhibit inconsistent electrical properties over the surface of the material.

There remains a need therefore, for a composite for use as a conductive polymeric material that provides electrical conductivity without compromising the desired properties of the polymeric material, and further, there is a need for conductive polymeric materials that provide consistent electrical characteristics.

SUMMARY

In accordance with an aspect, the invention provides a non-aqueous isotropic electrically conductive signal receptive composite including a continuous conductive material, with a top surface and a bottom surface with both surfaces substantially covered by a dielectric polymer material with a polar material within the dielectric polymer.

In accordance with another aspect, the invention provides a method of making a non-hydrogel, isotropically conductive, signal receptive material. The method includes providing a continuously conductive material which is substantially covered on both sides with the mixture of a dielectric polymer and polar material.

In accordance with another aspect, the invention provides a non-aqueous isotropic electrically conductive signal receptive composite including a continuous conductive material with a top surface and a bottom surface, both the top surface and the bottom surface including a polymeric material thereon, said polymeric material including a polar substituent attached to a polymer of the polymeric material.

In accordance with another aspect, the invention provides a signal receptive material including a polar material disbursed within a polymeric material, and a conductive material within the polymeric material, the conductive material extending in a length direction and a width direction that are each substantially greater than a thickness direction of the signal receptive material.

In accordance with a further embodiment, the invention provides a signal receptive fiber material including a polar material disbursed within a polymeric material, and a conductive material within the polymeric material, the conductive material being substantially coated by the polymeric material with the polar material disbursed therein.

BRIEF DESCRIPTION OF THE DRAWINGS

The following description may be further understood with reference to the accompanying drawings in which:

FIG. 12 shows an illustrative diagrammatic view of impedance testing results of a composite with no polar material;

FIG. 13 shows an illustrative diagrammatic view of impedance testing results of a composite with polar material;

FIG. 14 shows an illustrative diagrammatic view of impedance testing results of a composite with polar material and conductive material;

FIG. 16 shows an illustrative diagrammatic view of skin impedance test results of a composite electrode that includes conductive material and polar material;

FIG. 19 shows an illustrative diagrammatic view of ECG/EKG test results using the composite electrode of FIG. 16;

FIG. 22 shows an illustrative diagrammatic view of a composite material that includes carbon fiber as a conductive material;

FIG. 23 shows an illustrative diagrammatic top view of an electrode that includes the composite of FIG. 22;

FIGS. 24A-24C show illustrative diagrammatic partial views of a signal receptive composite that includes woven material (FIG. 24A), non-woven material (FIG. 24B), and matted of felted material (FIG. 24C)

The drawings are shown for illustrative purposes only.

DETAILED DESCRIPTION

In accordance with various aspects of the invention, a signal receptive composite is provided that includes a non-aqueous dielectric material and a polar material within the signal receptive composite. The composite also includes conductive material within the non-aqueous dielectric material that, in accordance with certain aspects, extends at least in an elongated direction that is at least as long as twice the thickness of the signal receptive composite. In accordance with various further aspects, the conductive material includes elements that extend in an elongated direction, wherein the elongated direction is at least as long as the thickness of the signal receptive composite. In accordance with further aspects, the conductive material includes elements that generally extend in the elongated direction wherein the conductive material itself is not straight, but is formed of lose or woven or non-woven or matted or felted bundles of fibers surrounded by the signal receptive composite. In accordance with further aspects, the conductive material includes a metal foil, mesh material, scrim material, or woven or unwoven metal wool material.

Figure 1:
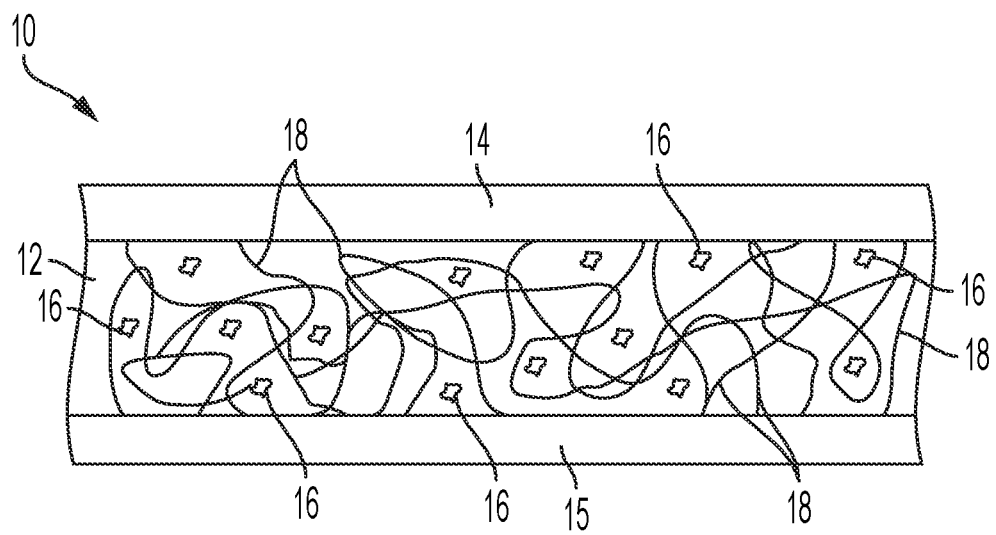
FIG. 1 shows an illustrative diagrammatic view of a composite in accordance with an aspect of the present invention.
Figure 2:
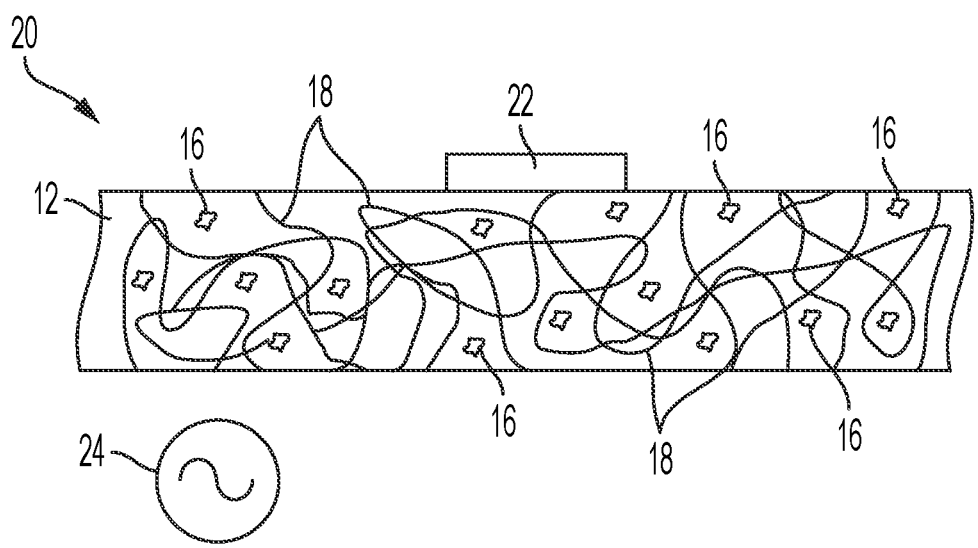
FIG. 2 shows an illustrative diagrammatic view of the composite of FIG. 1 applied to a subject.
Figure 3:
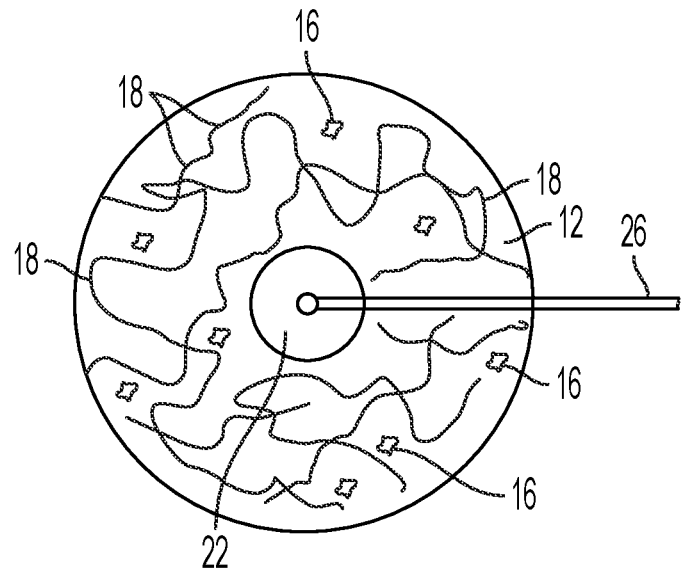
FIG. 3 shows an illustrative diagrammatic top view of an electrode including the applied composite of FIG. 2.

FIG. 1 shows at 10 a composite in accordance with an aspect of the present invention that includes a dielectric material 12 and a pair of release liners 14, 15 on either side thereof. The dielectric material 12 includes a polar material 16 therein, as well as conductive material 18 (e.g., referred to herein as a veil material). The conductive material (e.g., long strands of carbon fiber) may be randomly disbursed within the dielectric material in accordance with an aspect of the invention as shown in FIG. 1. With reference to FIG. 2, the release liners 14, 15 may be removed and a conductive electrode connection 22 may be applied to one side of the composite 20. When the opposite side of the composite 20 is applied to a subject (e.g., a patient), an alternating electrical signal (represented as 24) may be presented to the composite. Note that the electrical signal need not be directly below the electrode connection 22. FIG. 3 shows a top view of the composite 20, with the connection 22 coupled to a lead wire 26. The dielectric material 12 preferably has a surface energy that is low enough to wet out the surface of the conductive material 18, causing the surface of the conductive material (even exposed ends of the material 18 at the exposed surfaces thereof), to be covered by the dielectric material 12. Even the electrode connection 22 therefore, does not directly contact any of the conductive material 18 in accordance with an aspect of the invention.

In accordance with a particular aspect of the present invention, a polar material may be dispersed within the dielectric material, and may, for example, be (but is not limited to) a quaternary ammonium salt. There are a variety of such materials commercially available, mostly directed towards use as cationic surfactants or antistatic additives, as well as certain cosmetic applications. The variety of molecular variations in this family of compounds increases the odds of finding one that would be a compatible pairing to a given dielectric polymer as discussed in more detail below. Such a quaternary ammonium salt may be represented as:

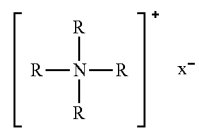

where R=H or some carbon based moiety, and where any of the R groups may be the same or different. For example, the polar material may be an Arquad HTL8-MS quaternary ammonium salt sold by Akzo Nobel Surfactants of Chicago, Ill.

The polymeric material may, for example, be but is not limited to, an acrylic adhesive such as may be represented as

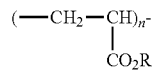

where R may vary and may be any of an ethyl, or a butyl or a 2-ethylhexyl or other organic moiety, and n is a number of repeating units. For example, the polymeric material may be a FLEXcon V95 pressure sensitive adhesive as sold by FLEXcon Company, Inc. of Spencer, Mass.

An objective of the selection of the combination of the binder material and the polar material in accordance with an aspect, is that the two materials each exhibit a mutual attraction that is very similar to the attraction that each material has to its own molecules. This results in the polar material being homogeneously dispersed within the binder material. The suitability of the combination of the polymeric material and the polar material may be identified by the following procedure. First, a polar material is combined with the polymeric material in about five different concentrations (typically between about 5% to about 45% by weight). Then the adhesive—salt composite is drawn onto a release liner (of about 1.5 mil), and permitted to dry and cure. The surface of the composite is then inspected after a short period of time. If the polar material has crystallized out or bloomed to the surface, then the combination of components is not compatible. If, on the other hand, the composite is clear, it is subject to the next level of compatibility testing. The samples should then be subjected an exposure test in which the samples are exposed to 100° F. with 95% relative humidity for 3 days. The samples are then again inspected to determine whether the polar material has migrated toward either surface. If there has been no migration of the polar material and the composite is clear, then the dielectric constant for the composite is determined and the composite is tested for use as a medical monitoring material.

The polymeric material and the polar material are therefore chosen in accordance with an aspect such that they each exhibit a mutual attraction that is substantially the same as the attraction to itself. Because of this, the polar material neither clumps together nor blooms to a surface of the polymeric material, but remains suspended within the polymeric material. This is in contrast to the use of salts in other applications wherein the salt is intended to bloom to the surface (to provide a conductive layer along a surface, e.g., for static discharge), or the salt is intended to chemically react with (e.g., dissolve into) the binder material. In other words, the binder material and the polar material are selected to be compatible but not such that they undergo a molecular change such as would occur, for example with NaCl in water. The molecule-scale polar material is therefore dispersed within the binder material but does not undergo a molecular transformation.

In accordance with further aspects of the present invention however, a polar material may be chosen such that the polar material may bind with a polymer of the dielectric material. In addition, therefore, in choosing a polymer (e.g., having a particular R group as discussed above) to have desired hydrophilic/hydrophobic characteristics, the polymer may further be chosen to bind to a particular polar material. The use of a dielectric material that includes a polar material bound to polymers of the dielectric material is advantageous where dissolution or blooming may occur over time. For example, if the polar material has an appropriate functional group, such as for example, a hydroxyl functional group, and the binder material has carboxyl groups, a reaction could occur where the polar material is to some degree incorporated in the binder material. In accordance with other aspects, if the binder material has ester pendent groups and the polar material has hydroxyl or even carboxyl functionality, some trans-esterification could occur, again, yielding polymer chains with attached polar material.

A PSA, for example, may include a cationic substituent of an acrylic copolymer. FLEXcon's V-19 adhesive (sold by FLEXcon Company, Inc. of Spencer, Mass.), for example, has a cationic substituent off an acrylic copolymer, PSA, which may bind to a polar material. In an example, this adhesive with a continuous conductive layer and no added polar material was provided. The continuous conductive layer was provided by a non-woven conductive veil product #20353A from Technical Fibre Products LTD, Schenectady, N.Y., The example was tested and yielded a skin impedance of 53 K ohms. The same adhesive and veil was then provided with half the normal loading of a polar material (e.g., FC-5000 ionic antistat material from 3M Company, Inc.), and the specimen yielded an impedance of 5.2 K ohms. This is a significant trade off, and other external considerations, such as skin adhesion are important considerations regarding a choice of a specific composition, but the use of cationic or other polar substituents to a polymeric material either a PSA to non-tacky layer affords more options in constructing the final signal receptive material (SRM).

One discernible feature of polymers that have such polar materials as a part of their structure is the relative permittivity. For example FLEXcon's H582 base adhesive has a relative permittivity at 100 Hz is 2.0; where the relative permittivity for FLEXcon's V-19 is 3.9. The relative permittivity indicates the polymer's possibility for use as a SRM even with the inclusion of a continuous layer, however other properties such as compatibility with the myriad of skin conditions will play a critical part of resin selection.

Figure 4:
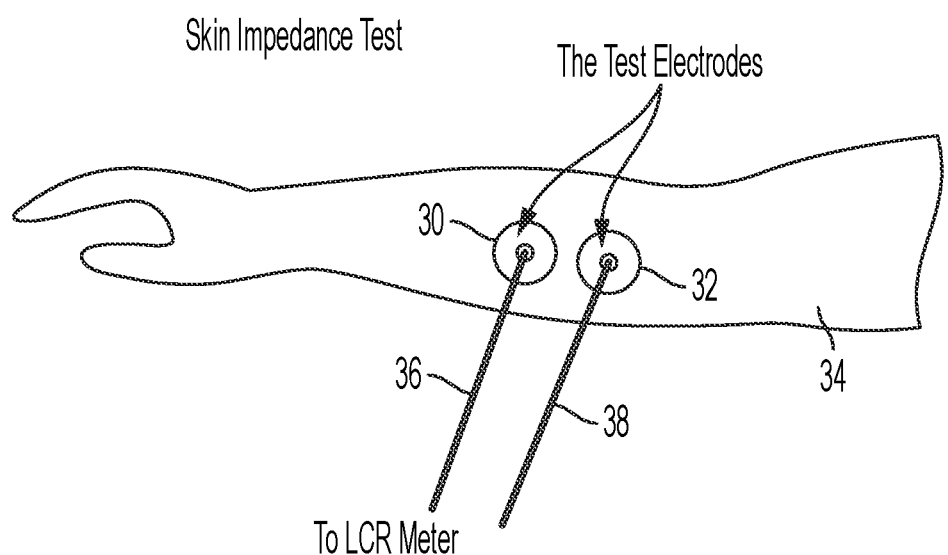
FIG. 4 shows an illustrative diagrammatic view of a pair or electrodes of FIG. 3 applied to a subject.

A test procedure was identified that could predict if a non-aqueous based SRM could perform in actual use in an ECG test (AAMI EC 12 2015 4.2.2 including 4.2.2.1, 4.2.2.2, 4.2.2.3, 4.2.2.4) and was found to be the skin impedance test. The skin impedance test involves, in part, applying a first test electrode to skin on an arm or a leg; starting a timer; applying a second test electrode to skin on the same arm or leg; attaching a voltmeter lead wires to the test electrodes; recording a measurement; and repeating for several minutes recording the results. With reference to FIG. 4, a pair of such electrodes 30, 32 may be placed near each other on a subject (e.g., an arm 34). Each electrode is coupled to a connection 36, 38 that connects to an inductance-capacitance-resistance (LCR) meter for determining skin impedance.

The non-aqueous composition provided herein in accordance with an aspect of the invention does not require bridging or activation to pass AMMI and is isotropic in accordance with an aspect of the invention. In an example, the composition includes a dielectric material, in which a polar compound is substantially dispersed within, and a conductive layer such as a fabric, woven or non-woven carbon fibers or a metallic screen or metallic foil material that is substantially covered with the material. The conductive continuous layers are available in various forms from carbon films, metallic foils, and screens to fabrics woven and non-woven and at several thickness and densities. The dielectric material can range in properties from pressure sensitive adhesives (PSAs) to non-tacky polymeric materials.

The polar material concentration may be as high as 45% by weight of the mixture with the dielectric polymer. The selection criteria of which polar material to go with which dielectric polymer is based on the compatibility with the organic dielectric as discussed above. Another attribute, where the dielectric polymer is a PSA, is that the ability of the material to adhere to the skin can be improved by proper selection of polar material. Which, given the large variation in surface qualities of skin, having the polar material that complements skin adhesion properties is a benefit.

The continuous conductive material may be introduced via coating, laminating, extruding, or any method for introducing a continuous or semi-continuous conductive layer within a polymer polar material blend. Further without the need to align or activate conductive particles even higher viscosity thermoplastic non tacky dielectric polymers are more easily incorporated into the SRM, which may find applications relating to the use of wearable bio-sensing electrodes held in place with wraps, vests or other such compression garments.

In accordance with an aspect, the invention provides a non-aqueous signal receptive material that is isotropic, and includes, for example, a continuous conductive layer within the dielectric material. The continuous conductive layer can be derived from conductive film, screen or a metallic foil, or, a conductive fabric, constructed of conductive fibers such as carbon fibers or non-conductive material with a conductive surface coating. The fabric can be either woven or knit or non-woven but in many examples the underlying principle is to have the resulting continuous conductive layer to be electrically conductive in at least the larger (X and Y) non-thickness dimensions, and optionally in all (X, Y, Z) dimensions. Being isotropic also facilitates connection to a backing electrical contact. Conversely, an anisotropic signal receptive material uses a conductive surface, which is connected via a conductive pathway to a monitor, wherein the area of that conductive surface directly relates to the amount of signal picked up. A composition consisting of a dielectric polymer with a polar material dispersed within, then including a continuously conductive material within the dielectric polymer will pass AMMI EC12 2015 without further processing steps such as bridging or activation. It has been found that when it comes to non-aqueous based signal receptive materials, skin impedance was a better predictor of function of the non-aqueous electrodes than just passing AAMI.

Figure 5A:
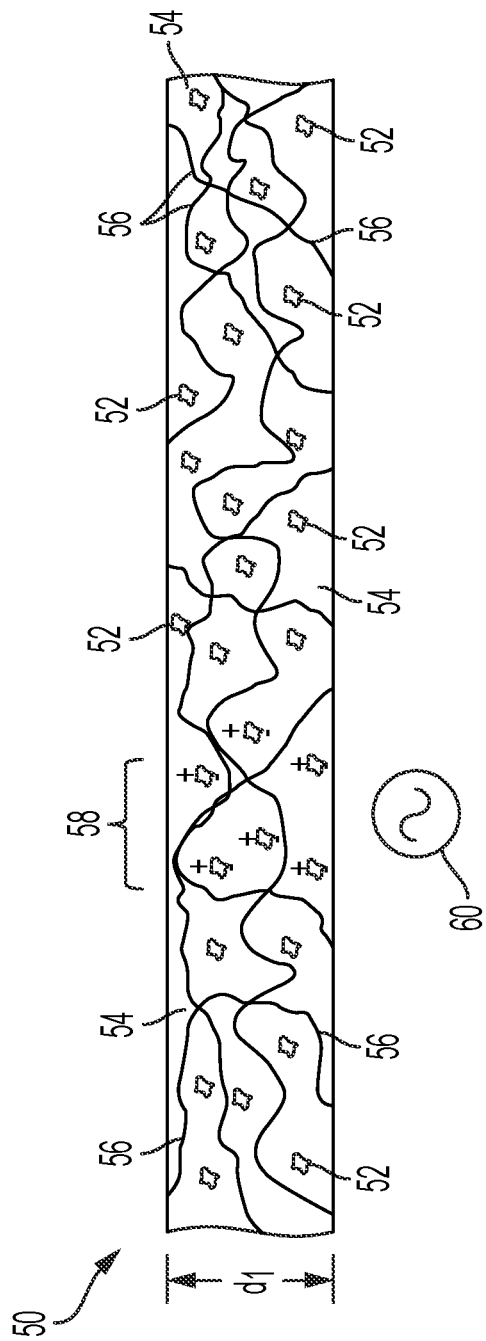
FIGS. 5A and 5B show illustrative diagrammatic views of a composite material in accordance with an aspect of the invention in the presence (FIG. 5A) and subsequent absence (FIG. 5B) of a charge from an alternating electric field.
Figure 5B:
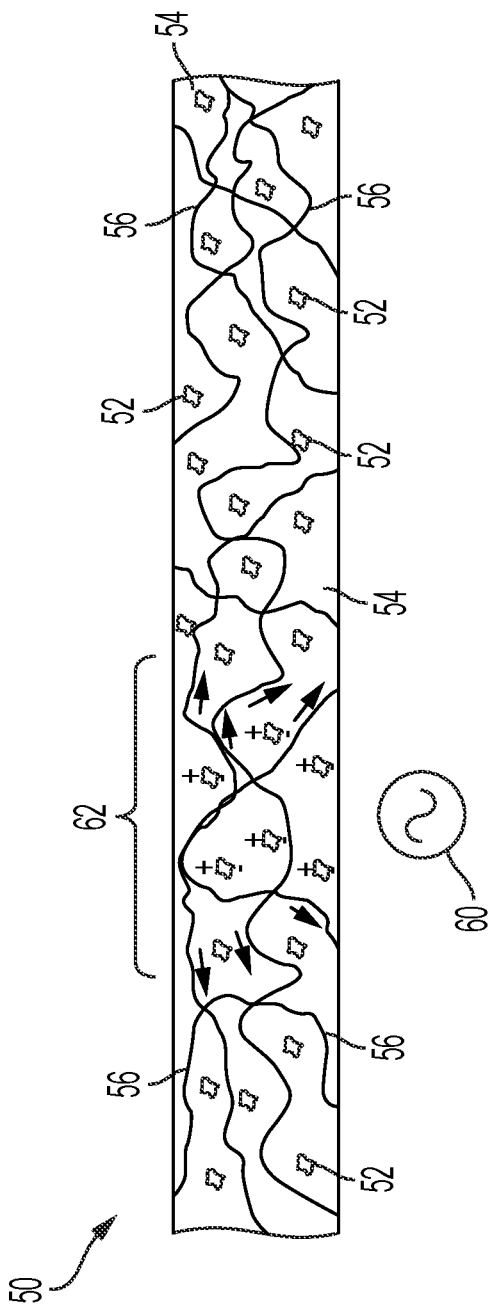

The mechanism by which an electrical signal is conveyed is dynamic, involving both capacitive coupling and. a low impedance conductive material such as a conductive veil or other continuous conductive layer as discussed herein. With reference to FIGS. 5A and 5B, a composite 50 in accordance with an aspect of the invention includes a polar material 52 disbursed within a dielectric material 54 as well as a conductive material 56 as discussed above. The thickness of the composite $d_1$ may vary widely in accordance with a variety of biomedical non-biomedical uses, and may, for example be as thin as order of microns, or may be over an inch in thickness, again depending on the application. The diameter of the carbon fibers 56 may, for example less than 1 micrometer or greater than 50 micrometers, again depending on the application. While the polar material (shown at 58 in FIG. 5A) proximate a signal source 60 will react to the alternating signal, polar material that is not proximate the source will not so react. In accordance with an aspect of the present invention however, the conductive material 56 will pick up the signal and distribute the signal throughout the composite via charge distribution as shown with arrows in the area 62 of FIG. 5B.

Figure 6:
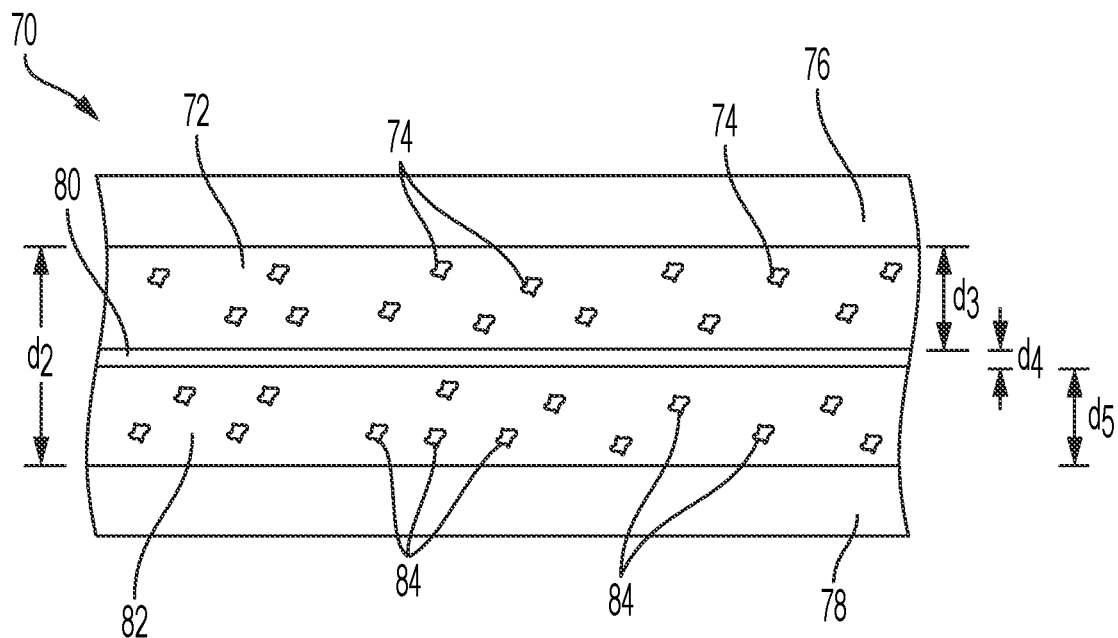
FIG. 6 shows an illustrative diagrammatic view of a composite in accordance with another aspect of the present invention that includes a continuous conductive material.
Figure 7:
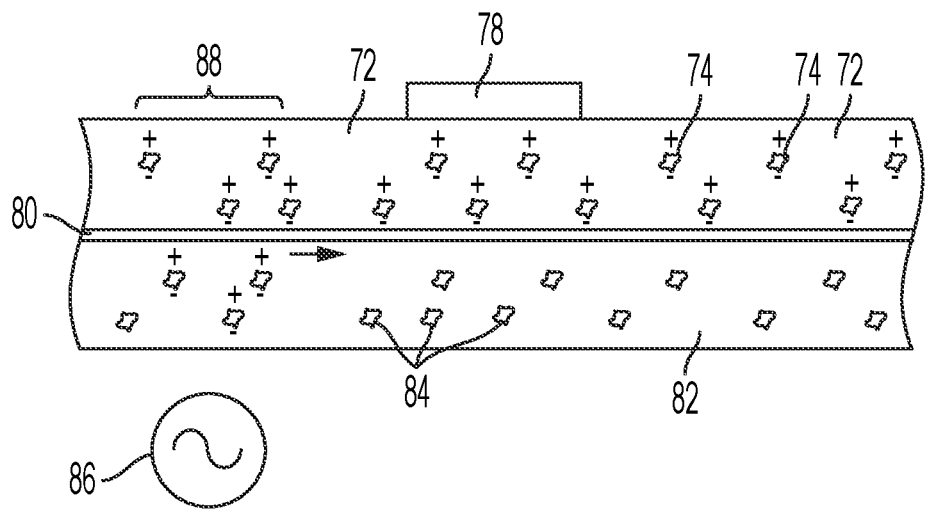
FIG. 7 shows an illustrative diagrammatic view of the composite of FIG. 6 in the presence of an alternating electric field.
Figure 9:
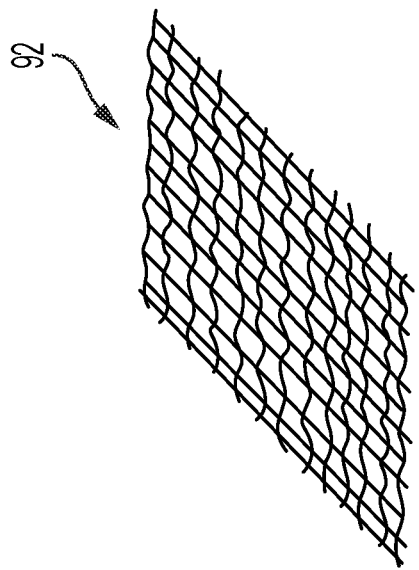
FIG. 9 shows an illustrative diagrammatic view of a continuous conductive material in the form of a woven material in accordance with an aspect of the present invention.
Figure 11:
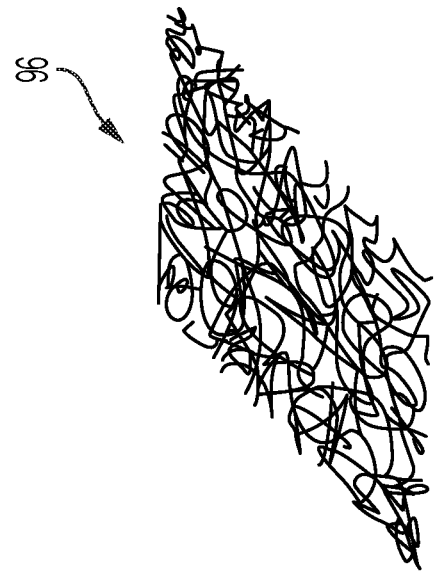
FIG. 11 shows an illustrative diagrammatic view of a continuous conductive material in the form of a non-ordered material in accordance with an aspect of the present invention.
Figure 8:
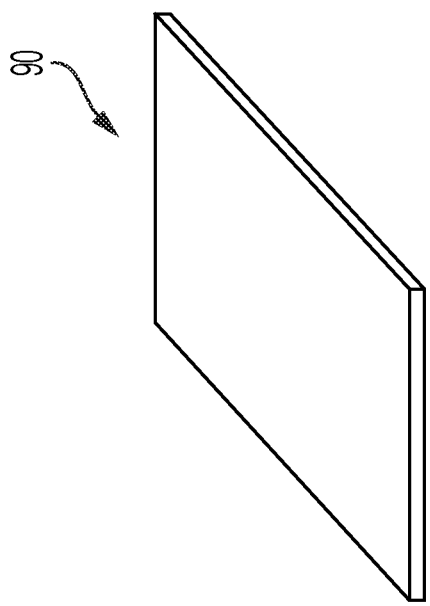
FIG. 8 shows an illustrative diagrammatic view of a continuous conductive material in the form of a solid film in accordance with an aspect of the present invention.
Figure 10:
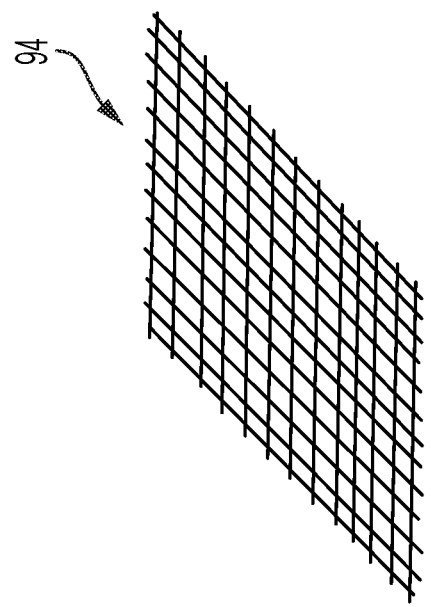
FIG. 10 shows an illustrative diagrammatic view of a continuous conductive material in the form of a non-woven grid material in accordance with an aspect of the present invention.

As mentioned above, the continuous conductive material may comprise a layer of conductive material that is provided as a layer of a conductive film (e.g., aluminum or carbon), a layer of a woven or non-woven material (e.g., carbon fibers), or a flattened mat of non-ordered material (again, e.g., carbon fibers). With reference to FIG. 6, such a conductive material layer may be provided between two layers of the dielectric material with the polar material disbursed therein. In particular, the composite 70 includes a first dielectric material 72 with a polar material 74 disbursed therein, and a second dielectric material 82 with a polar material 84 disbursed therein, as well as a conductive layer 80 sandwiched between the first dielectric material 72 and the second dielectric material 82. The composite 70 further includes release liners 76, 78 on exposed surfaces of the composite. The composite (without the release liners) may have a thickness $d_2$, the first dielectric material 72 may have a thickness $d_3$, the second dielectric material 82 may have the thickness of $d_5$, and the conductive layer 80 may have a thickness $d_4$, again all suited to the particular application. A benefit of aspects of the invention is that composites of the invention are highly versatile in applications requiring a wide variety of thicknesses or other dimensions. With reference to FIG. 7, when in the presence of an alternating signal (e.g., a biomedical signal as shown at 86), certain of the polar material (as shown at 88 in FIG. 7) will align with the biomedical signal. The resulting charge from this alignment will be picked up by the conductive layer 80 and transferred about the composite, causing additional polar material 74 to become aligned as shown in FIG. 7. This resulting additional polar material being aligned will cause a signal to be provided to the electrode 78. With reference to FIGS. 8-11, the conductive layer 80 may be any of a film 90 (e.g., of aluminum or carbon), a metal fabric of woven conductive material 92 (e.g., woven carbon fiber), a non-woven grid 94 (e.g., of carbon fiber), or a flattened mat of non-ordered material 94 (again, e.g., carbon fibers).

The following examples show composites made in accordance with various aspects of the present invention.

EXAMPLE 1

To a solution of organic solvents of a PSA, (FLEXcon's H-582 sold by FLEXcon Company, Inc. of Spencer, MA) is added a polar material at 15% by dry weight, of, in this example, Arquad HTL8-MS sold by Nouryon Chemicals of The Netherland. The solution was cast on the release coated side of a 38 micron polyester film. To this, a continuous conductive layer material was applied. In this example, the continuous conductive layer was a non-woven conductive veil material, product # 20352A at 4 g/sm available from Technical Fibre Products LTD., Schenectady, NY. The veil material was laid on and pressed into the still wet PSA solution. The composite was then dried. Then a second sample was prepared in a similar fashion, using the same pressure sensitive adhesive and the same veil material, but without including any polar material.

The two samples, one with and one without polar material and, together with a conventional aqueous based ECG electrode (the Silver Mactrode Plus made by GE Healthcare, Inc. of Marlborough, MA) acting as a control reference, were all tested in accordance with AAMI EC12 2015 4.2.2.1, 4.2.2.4 and 4.2.2.2, 4.2.2.3 and 4.2.2.5 and the above referenced skin impedance test. The results are shown in FIGS. 12-14, wherein FIG. 12 shows at 100 the results for the Silver Macrode, FIG. 13 shows at 102 the results for the composite without the polar material (FLEXcon's H-582 and the Carbon Veil 20352A, with no polar material), and FIG. 14 shows at 104 the results for the composite with the polar material (FLEXcon's H-582, polar material (Arquad HTL8-MS) and Carbon Veil 20352A). As shown, each of the electrodes passed all of the components of the applicable AAMI EC12 2015 test.

Figure 15:
FIG. 15 shows an illustrative diagrammatic view of skin impedance test results of an electrode that includes silver (Silver Macrode)
Figure 17:
FIG. 17 shows an illustrative diagrammatic view of skin impedance test results of a composite electrode that includes conductive material and no polar material.

When these three samples were tested with FLEXcon's Skin Impedance test noted above with reference to FIG. 4 however, the results diverged. The Silver Mactrode and the sample with both the veil conductive material and the polar material, easily passed. The sample with just the veil conductive material added to the adhesive, with no polar material resulted in skin impedance an 8 fold multiple higher than the sample with the addition of the polar material. In particular, FIG. 15 shows at 106 the results of the skin impedance test of the Silver Macrode, FIG. 16 shows at 108 the results of the skin impedance test of the composite with the polar material, and FIG. 17 shows at 110 the results of the skin impedance test of the composite without the polar material, showing substantially increased impedance when the polar material is omitted.

Figure 18:
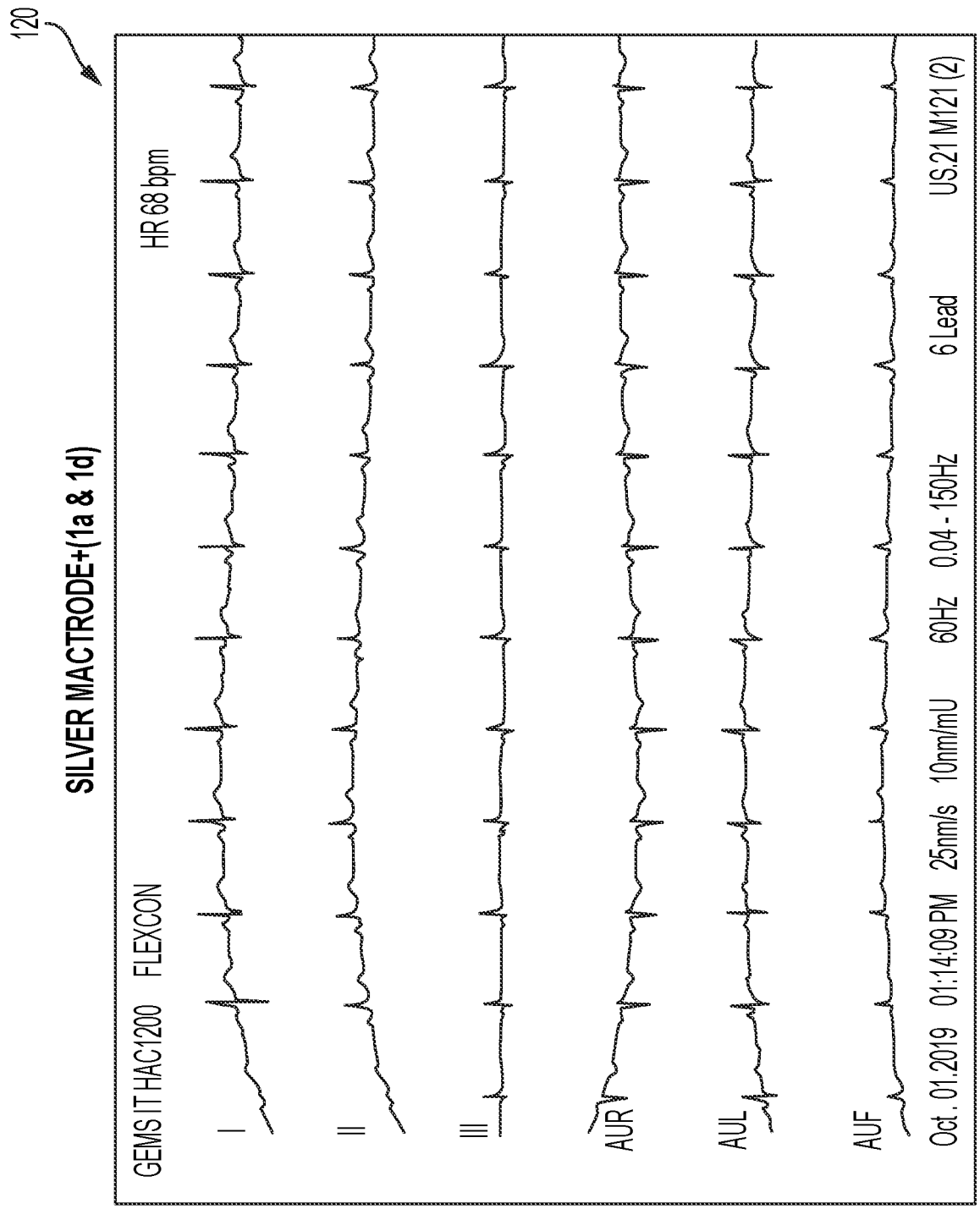
FIG. 18 shows an illustrative diagrammatic view of ECG/EKG test results using the electrode of FIG. 15.
Figure 20:
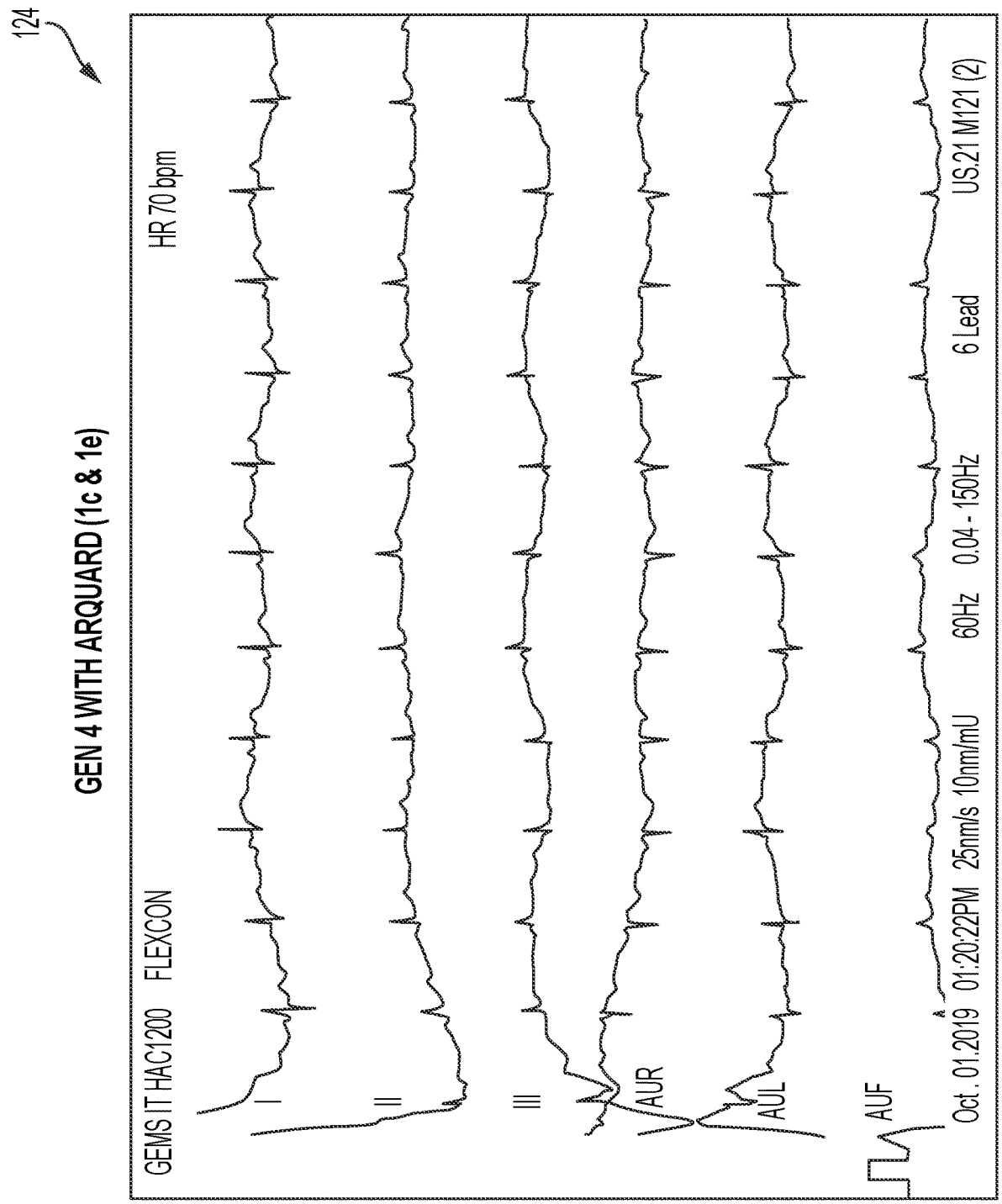
FIG. 20 shows an illustrative diagrammatic view of the ECG/EKG test results using the composite electrode of FIG. 17.

These three electrodes were also tested on a MAC 1200G ECG/EKG machine from GE Healthcare, Inc. The results are shown at 120 in FIG. 18 for the Silver Macrode electrode, at 122 in FIG. 19 for the composite without the polar material, and at 124 in FIG. 20 for the composite with the polar material. Clearly, the polar material is required as FIG. 19 shows no detected ECG signals, and show that the composite with the polar material provided excellent ECG signal data.

Subsequent processing of the signal receptive material with the continuously conductive material and the polar material is very efficient due to the isotropic conductive nature of the composite. Besides not requiring bridging or activation, the substrate to which the signal receptive material is attached does not require that the entire surface of the substrate (that comes in contact with the signal receptive material) be electrically conductive.

For example, to a supporting substrate (FLEXMARK NWP non-woven polyester sold by FLEXcon Company, Inc. of Spencer, MA) was applied a signal receptive material consisting of a dielectric polymer (H-582 sold by FLEXcon Company, Inc.) and 30% by weight a polar material (Ionic Liquid Antistat FC-5000, which is a salt of alkoxylated quaternary alkyl ammonium fluoroalkylsulfonimide, sold by 3M Company, Inc. of St. Paul, MN), and a conductive material (Optiveil 20352A carbon fiber material sold by Technical Fibre Products LTD of the United Kingdom). A second sample was similarly prepared with the addition of a conductive outer coating (EXV-461 conductive coating sold by FLEXcon Company, Inc.) on the same side of the supporting substrate that the signal receptive material would be added; this conductive coating would be necessary with the anisotropic signal receptive material of the prior art.

Figure 21:
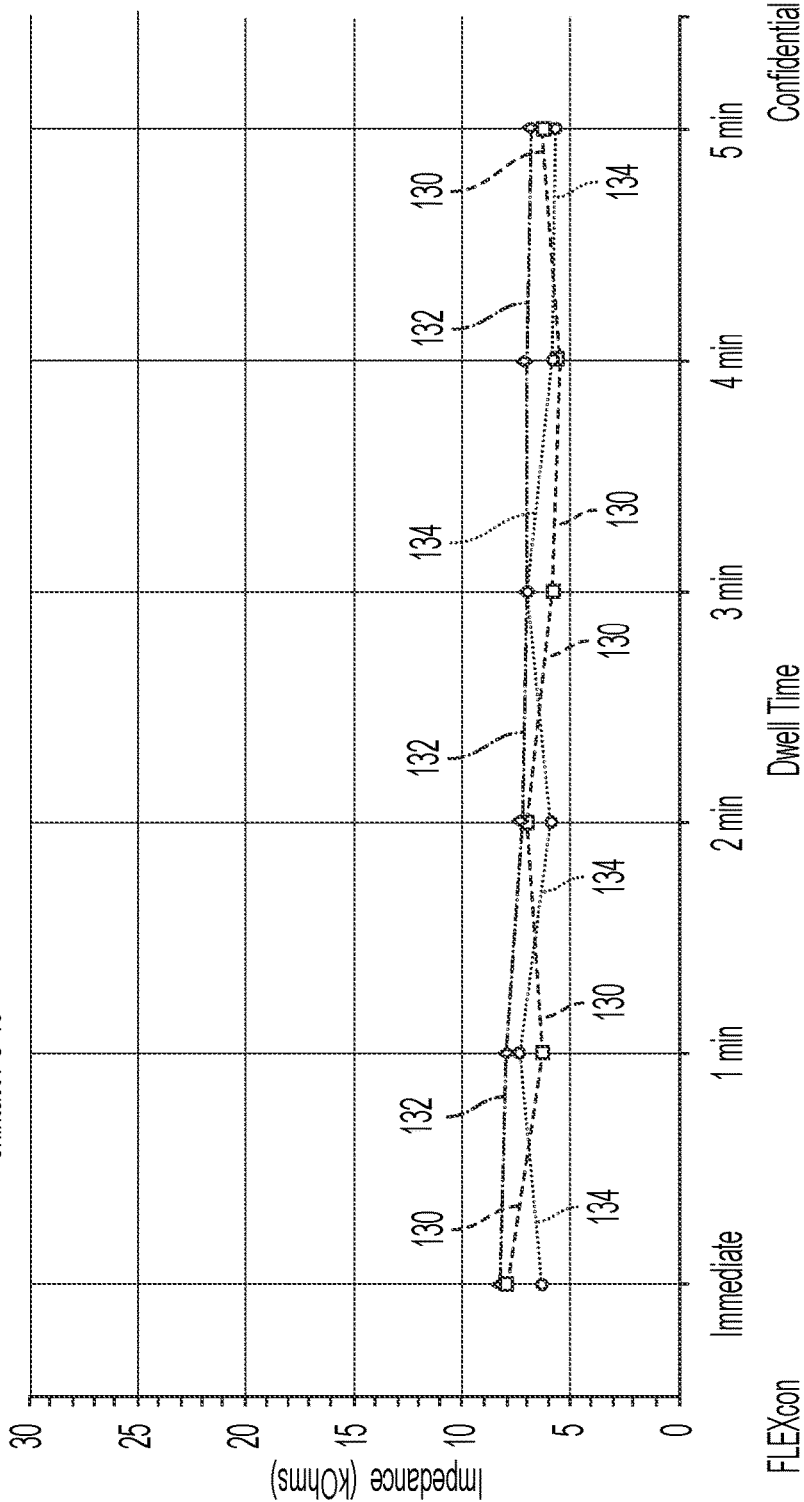
FIG. 21 shows an illustrative diagrammatic view of electrode to skin impedance using ECG snap electrodes with and without polar material, together with a test control electrode.

To both samples, ECG snap electrodes were installed and tested for skin impedance. An aqueous electrode material (Skintact FS-40 sold by Leonard Long USA, Inc. of Iverness, FL) was also tested as a control. With reference to FIG. 21, no substantial differences in electrode-to-skin impedance was found between the aqueous electrode control and the electrodes without (shown at 130) or with (shown at 132) a conductive coating over the supporting substrate under the signal receptive material, or the Skintact electrode (shown at 134). This means that virtually little to no change in subsequent manufacturing steps would be needed between the current product and the isotropically conductive non-aqueous signal receptive material. A further advantage is that in most aqueous snap electrodes the hydrogel is surrounded by an adhesive to affix the electrode to the skin. In accordance with aspects of the present invention, the signal receptive material is also the adhesive.

Yet another advantage of using the continuously conductive layer, is that since there is no activation step the base adhesive need not be of high viscosity (over 1 million cps) to maintain the electrophoretic formed "Z" columns. This allows for other lower viscosity PSAs such as radiation curable PSAs. Using a low viscosity radiation curable PSA with conductive particles would require a reasonably strong electric field for materials like carbon or if a ferromagnetic particles are used a magnetic field. In either event an anisotropic signal receptive material would be the result. Using a veil with a radiation curable PSA, the limiting factor is the curing as there is no alignment of particles required and the resulting product is isotropic.

EXAMPLE 2

To 100 parts of adhesive (Rad Bond 12 PS 12L V FB adhesive sold by Actega North America, of Chicago, IL) were added 5 parts of polar material (Arquad HTL8-MS, sold by Nouryon Chemicals of The Netherlands. The mixture was coated on Carbon Veil 20352A sold by Technical Fibre Products Inc. of Schenectady, NY, supported on a 90 poly flat white (PFW) release liner, sold by FLEXcon Company, Inc. Samples so constructed were cured under a UV lamp, then laminated to a conductive carbon coated 50 micron polyester. A second set of samples were similarly prepared but in this case no polar material (Arquad HTL8-MS) was added.

Both sets of samples were tested by placing on conductive carbon filled acrylic. Contact was made to the conductive coated 50 micron polyester base and the conductive island placed on the opposite side of the SRM and tested. The electrode-to-electrode impedance results were as follows: with the polar material the impedance was 1.5 K ohms, and without the polar material the impedance was 420 ohms. Next the samples were tested for skin impedance, and the control (silver mactrode) had an impedance of 4 K ohms, the sample with the polar material (Arquad) had an impedance of 19 K ohms, and the sample without the polar material (Arquad) had an impedance of 380 K ohms.

Note that while the electrode to electrode impedance shows that the sample without Arquad (polar material) had a lower impedance than the electrode with the Arquad, the skin impedance test shows that, just as in the previous example, the results were reversed. Similar composites using aluminum foil, metallic fine screen material and a conductive woven fabric were also fabricated and all exhibited the isotropic property found with the nonwoven veil material.

EXAMPLE 3

The third example involved the use of a metallic foil such as an Aluminum foil to explore how thin an electrode can be prepared. Being flat, aluminum foil avoids the irregular profile of fabrics, both woven and non-woven. To a 0.0007 inch aluminum foil was applied a mixture of a polar compound (FC-5000 sold by 3M Company, Inc.) and pressure sensitive adhesive (PSA H-582) sold by FLEXcon Company, Inc. This blend was coated on the aluminum foil to a coating deposition (dry) of 0.0002 inches and covered with a silicone coated polyester to protect the adhesive composition. To the opposite side of the Aluminum/PSA/protective liner composite a second coating of the adhesive/polar material is applied, again to a dry deposit on of 0.0002 inches. Samples of the above composite were tested for impedance in both the thickness (Z) and length, width (X,Y) dimensions. The average impedance in the Z direction was 540 ohms, and the average impedance in the X,Y plane was 590 ohms. These values are well within a definition of electrically isotropic.

In accordance with further aspects, the continuous polymeric medium may not be a pressure sensitive adhesive (e.g., it may be a substantially non tacky material). Such electrodes are often used in combination with compression garments. In many, but not all cases, the non-tacky electrode is permanently attached to said compression garments, thus making repeated washing survivability a criteria for many possible applications. Thus the water solubility of any polar material within a continuous polymer matrix should be minimized. Another consideration is that the moisture vapor transmission rate of the electrode should be such as to minimize the buildup of perspiration between the skin and the electrode.

In a further example, a composite was formed where the continuous, substantially non tacky layer of a thermoplastic polyurethane (TPU) (H-501 sold by FLEXcon Company, Inc.) containing a polar material (FC-5000 sold by 3M Company, Inc.) 15% by dry weight, as well as a veil material (Optiveil 20352A sold by Technical Fibre Products LTD). As in the case of the example with a PSA as the dielectric continuous layer, a solution of the TPU resin and the FC 5000, are coated on a releasable carrier film, with the veil the composite is then dried. Test strips were then prepared and for skin impedance testing using a 60 g weight to apply pressure to the skin. The results yield a Skin impedance of 40 K ohms.

To affix the non-tacky test bio-signal sensing material to a compression fabric, the TPU resin could adhere to many fabrics merely heating the non-coated side of the releasable carrier. With both the non-tacky layer and the garment compatible, a bond can be formed. In the cases where the fabric is not compatible with the continuous layer in the sensor an additional layer of material over the SRM would need to be added to facilitate bonding.

In accordance with further aspects of the invention, the signal receptive composite may be used for a wide variety of applications, biomedical and otherwise, when the passing of a signal from one area to another is required. Certain applications, for example, may not even require that the polymeric material be an adhesive. Further, it is not required that the composite of the invention be provided as a pad or traditional electrode.

For example, in accordance with further aspects of the invention, the conductive material may include carbon fibers, and the carbon fibers may be coated with a dielectric material that includes a polar material disbursed therein as discussed above. FIG. 22, for example, shows a signal receptive composite 150 that includes a carbon fiber as the conductive material 152, as well a coating of a dielectric material 158 with a polar material 156 disbursed therein. As shown in FIG. 23, the dielectric material 154 (including the dielectric material 158 and the polar material 156) surrounds the conductive material fiber 152.

With further reference to FIG. 24A, such a signal receptive composite 150 may be used to form a woven composite 160 by weaving multiple such coated fibers 150 together. Similarly, as shown in FIG. 24B, such a signal receptive composite 150 may be used to form a non-woven composite 162 by combining multiple such coated fibers 150 in a non-woven fashion. As shown in FIG. 24C, such a signal receptive composite 150 may be used to form a matted or felted composite 164 by combining multiple such coated fibers 150 in a matted or felted fashion.

A further use of an isotropic SRM material in accordance with various aspects of the invention involves delivering electronic pulses to a subject. For example, the use of Transcutaneous Electrical Nerve Stimulation (TENS) may be used for a variety of applications, including reducing pain. TENS units deliver small electrical impulses through the electrodes to a patients skin, and these electrical impulses stimulate the body to produce endorphins which may (in certain specific applications) reduce pain.

An example of such a composite included FLEXcon dry electrodes with FLX068983 OMNI-WAVE™ TT 200 and BLACK H-502, was provided together with an example including Silver Mactrode™ Plus hydrogel electrodes. The testing equipment included as a signal source, a iReliev iRenew™ TENS+EMS System—Model # ET-7070, and as a signal monitor—Tektronix MDO3024 Oscilloscope & leads with clips. A testing methodology involving an electrode pair assembly involved providing that a protective release liner was removed from the adhesive side on each of two electrodes. The adhesive layers of each electrode were then placed together forming an electrode pair. A testing methodology for an electrode signal test involved an electrode pair that was connected to the measuring equipment. Signal measurements were collected two minutes after electrode pair assembly. A testing methodology for an electrode impedance test involved an electrode pair that was connected to the LCR meter. Impedance measurements were taken at 10 hz 20 mv two minutes after electrode pair assembly.

Figure 25:
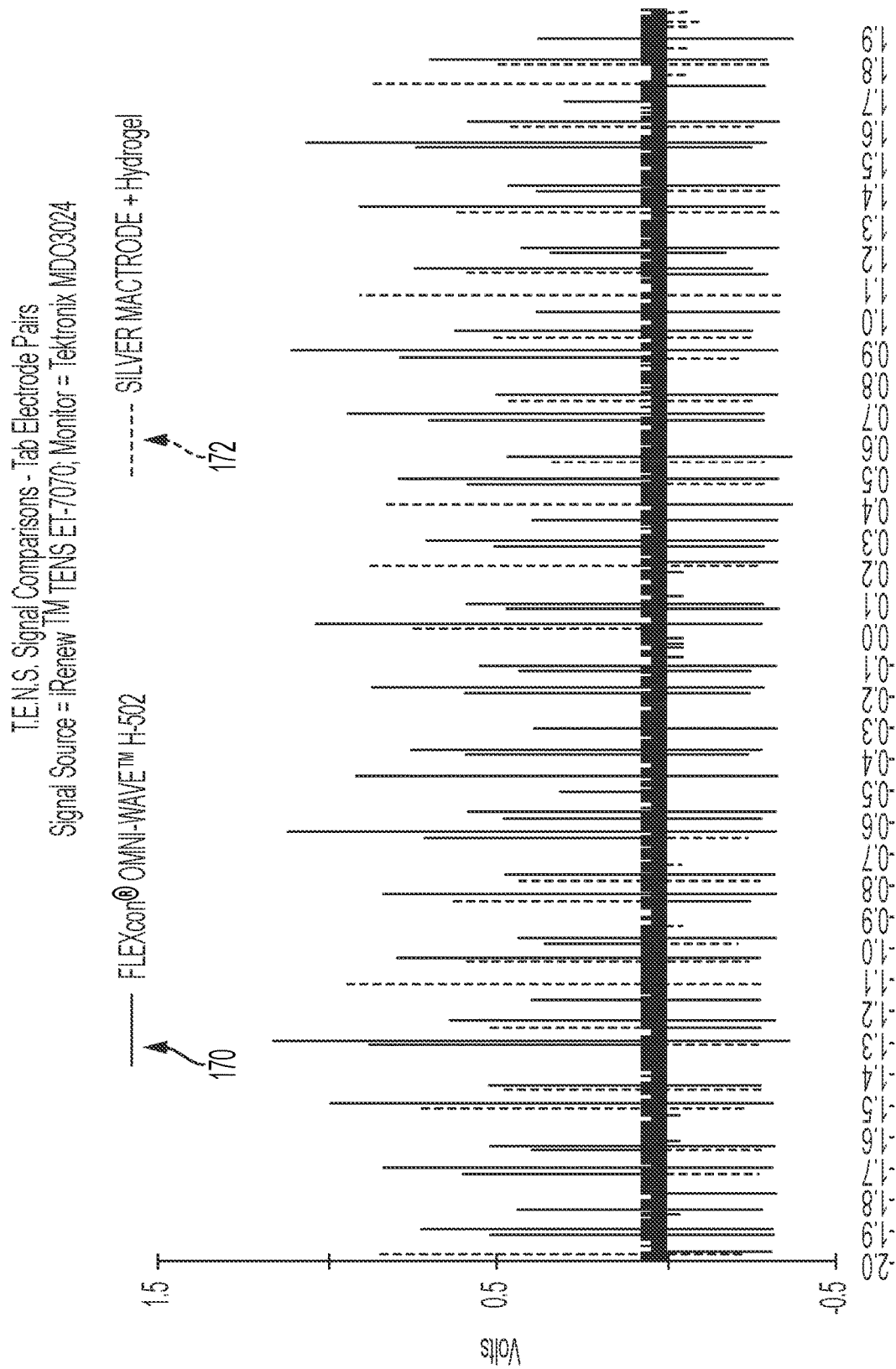
FIG. 25 shows an illustrative diagrammatic signal comparison view of transcutaneous electric nerve stimulation (TENS) testing in a composite in accordance with an aspect of the invention as well as in a composite that includes silver (Silver Macrode).

The measurements were as follows. For the electrode pair impedance the, the Silver Mactrode™ Plus yielded an impedance of 444 ohms, and for the SRM composite (FLEXcon® OMNI-WAVE™ H-502) yielded an impedance of 139 ohms. For the electrode signal test (and with reference to FIG. 25), the impedance for the SRM composite is shown at 170, and the impedance for the Silver Macrode plus hydrogel is shown at 172. The measured voltage and impedance of the FLEXcon dry electrodes with OMNI-WAVE™ H-502 are similar to or better than the Silver Mactrode+(hydrogel) electrodes.

Those skilled in the art will appreciate that numerous modifications and variations may be made to the above disclosed embodiments without departing from the spirit and scope of the present invention.

What is claimed is:

1. A non-aqueous isotropic electrically conductive signal receptive composite comprising a dielectric polymer material with a polar material substantially dispersed within the dielectric polymer material, said polar material being responsive to an alternating electric signal outside of the signal receptive composite to provide a polar discharge response within the signal receptive composite, and a continuous conductive material within the dielectric polymer material and extending substantially throughout the signal receptive composite, said continuous conductive material being receptive of the polar discharge response for distribution throughout the signal receptive composite, said signal receptive composite including a top surface and a bottom surface with both surfaces substantially covered by the dielectric polymer material with the polar material dispersed therein.

2. The composite as claimed in claim 1, wherein the dielectric polymer material and the polar material do not exhibit substantial phase separation, even after exposure to high humidity.

3. The composite as claimed in claim 1, wherein the polar material has a concentration of up to 45% by weight of the dielectric polymer material with the polar material, and the polar material and is substantially dispersed within said dielectric polymer material.

4. The composite as claimed in claim 1, wherein the dielectric polymer material is a PSA.

5. The composite as claimed in claim 4, wherein the PSA is based on an acrylic copolymer.

6. The composite as claimed in claim 1, wherein the dielectric polymer material is a non-tacky polymer.

7. The composite as claimed in claim 6, wherein the non-tacky dielectric polymer material is a thermoplastic urethane.

8. The composite as claimed in claim 1, wherein the polar material is from the family of quaternary ammonium salts.

9. The composite as claimed in claim 1, wherein the continuous conductive material is a conductive fiber nonwoven.

10. The composite as claimed in claim 1, wherein the continuous conductive material is a woven fabric consisting of conductive carbon fiber yarn.

11. The composite as claimed in claim 1, wherein the continuous conductive material includes metallic foil.

12. The composite as claimed in claim 11, wherein the continuously conductive layer includes aluminum foil.

13. The composite as claimed in claim 1, wherein the continuous conductive material is a conductive screen.

14. A non-aqueous isotropic electrically conductive signal receptive composite comprising a polymeric material with a polar material substantially dispersed within the polymeric material, said polar material being responsive to an alternating electric signal outside of the signal receptive composite to provide a polar discharge response within the signal receptive composite, and a continuous conductive material within the polymeric material and extending substantially through the signal receptive composite, said continuous conductive material being receptive of the polar discharge response for distribution throughout the signal receptive composite, said signal receptive composite including a top surface and a bottom surface, both the top surface and the bottom surface including the polymeric material thereon, said polymeric material including the polar material attached as a substituent to a polymer of the polymeric material.

15. The non-aqueous isotropic electrically conductive signal receptive material as claimed in claim 14, wherein the polymeric material further includes polar material substantially dispersed therein.

16. The non-aqueous isotropic electrically conductive signal receptive material as claimed in claim 14, wherein the polymeric material includes a cationic substituent attached to the polymer.

17. The non-aqueous isotropic electrically conductive signal receptive composite as claimed in claim 14, wherein the polymeric material includes an anionic substituent attached to the polymer.

18. A non-aqueous isotropic signal receptive material composite comprising a polar material substantially disbursed within a polymeric material, said polar material being responsive to an alternating electrical signal outside of the signal receptive material composite to provide a polar discharge response within the signal receptive material composite, and a conductive material within the polymeric material and extending substantially throughout the signal receptive material composite, said conductive material being receptive of the polar discharge response for distribution throughout the signal receptive material composite, and said conductive material extending in a length direction and a width direction that are each substantially greater than a thickness direction of the signal receptive material composite.

19. The non-aqueous isotropic signal receptive material composite as claimed in claim 18, wherein the conductive material includes veil of carbon fibers.

20. The non-aqueous isotropic signal receptive material composite as claimed in claim 18, wherein the conductive material includes a fabric of carbon fibers.

21. The non-aqueous isotropic signal receptive material composite as claimed in claim 18, wherein the conductive material includes a metal foil.

\* \* \* \* \*